(12) United States Patent
Knoth

(10) Patent No.: US 7,426,814 B2
(45) Date of Patent: Sep. 23, 2008

(54) METHOD OF DISPENSING PILLS FROM A MOVABLE PLATEN

(75) Inventor: Norman D. Knoth, Clearwater, FL (US)

(73) Assignee: QEM, Inc., Largo, FL (US)

( * ) Notice: Subject to any disclaimer, the term of this patent is extended or adjusted under 35 U.S.C. 154(b) by 0 days.

(21) Appl. No.: 11/683,871

(22) Filed: Mar. 8, 2007

(65) Prior Publication Data
US 2007/0157548 A1 Jul. 12, 2007

Related U.S. Application Data

(63) Continuation-in-part of application No. 11/318,186, filed on Dec. 23, 2005, now Pat. No. 7,225,597.

(51) Int. Cl.
*B65B 1/04* (2006.01)
(52) U.S. Cl. ............... 53/473; 53/475; 53/244; 53/246; 53/249
(58) Field of Classification Search ............ 53/473, 53/475, 244, 245, 246, 247, 249; 221/92, 221/94
See application file for complete search history.

(56) References Cited

U.S. PATENT DOCUMENTS

| 2,457,220 | A | * | 12/1948 | Fowler et al. ............ 53/244 |
| 2,618,420 | A | * | 11/1952 | Levine ................... 53/247 |
| 3,080,033 | A | * | 3/1963 | Graeme et al. ............ 193/23 |
| 3,139,713 | A | * | 7/1964 | Merrill et al. .............. 53/246 |
| 3,677,437 | A | | 7/1972 | Haigler |
| 3,775,941 | A | * | 12/1973 | Bross ..................... 53/246 |
| 3,789,575 | A | * | 2/1974 | Bross ..................... 53/246 |
| 5,522,512 | A | | 6/1996 | Archer et al. |
| 5,761,877 | A | | 6/1998 | Quandt |
| 5,771,657 | A | | 6/1998 | Lasher et al. |
| 5,799,468 | A | * | 9/1998 | Eck et al. ................. 53/473 |
| 5,873,488 | A | * | 2/1999 | Guerra .................... 221/220 |
| 5,897,024 | A | | 4/1999 | Coughlin et al. |
| 6,269,612 | B1 | * | 8/2001 | Aylward ................... 53/473 |
| 6,318,051 | B1 | | 11/2001 | Preiss |
| 6,363,687 | B1 | * | 4/2002 | Luciano et al. ............ 53/55 |
| 6,497,083 | B1 | * | 12/2002 | Garwood et al. .......... 53/244 |
| 6,578,734 | B1 | | 6/2003 | Coughlin et al. |
| 6,581,356 | B2 | * | 6/2003 | Kim ...................... 53/154 |
| 6,658,135 | B1 | * | 12/2003 | Morito et al. ............. 382/100 |
| 6,805,259 | B2 | | 10/2004 | Stevens et al. |
| 6,925,774 | B2 | * | 8/2005 | Peterson .................. 53/247 |
| 7,174,694 | B2 | * | 2/2007 | Ogger et al. ............... 53/246 |
| 7,182,105 | B1 | | 2/2007 | Feehan et al. |

* cited by examiner

*Primary Examiner*—Louis K Huynh
(74) *Attorney, Agent, or Firm*—Larson & Larson; Frank Liebenow (57) ABSTRACT

A plurality of cassettes, each filed with a supply of pills and positioned over a target location. A platen is provided beneath the target location with receptacles configured to hold both vials and blister packs. The platen or the cassette is movable so that any blister of the blister pack or the vial can be positioned under the target location to receive a quantity of pills from the cassette.

6 Claims, 9 Drawing Sheets

METHOD OF DISPENSING PILLS FROM A MOVABLE PLATEN

PRIOR APPLICATIONS

This application is a continuation-in-part of application Ser. No. 11/318,186, filed on Dec. 23, 2005 now U.S. Pat. No. 7,225,597.

BACKGROUND OF THE INVENTION

1. Field of the Invention

The present invention relates to the field of dispensing medicine and more particularly to an apparatus that automatically fills vials and blister packs with medicine in the form of pills, capsules, gel-caps and the like.

2. Description of the Related Art

The dispensing of medicine in the form of pills, capsules, gel-caps, and the like is performed in many ways and in many locations including pharmacies, packaging plants and hospitals. Pharmacies or drug stores employ Pharmacists to fill prescriptions with the prescribed amount of a prescribed medicine or dose. The Pharmacist fills the prescription from a bulk package of medicine into a delivery package sized for the consumer. Although Pharmacists are very careful to dispense the correct quantity of the correct medicine, ever too often, the wrong quantity is dispensed, or worse yet, the wrong medicine is dispensed.

The medicine is often delivered to the consumer in a package that is a container with a lid, for example, a vial or bottle. After counting the prescribed amount of medicine, the Pharmacist funnels the pills into the container, attaches the lid and places a label on the container indicating what medicine is stored inside and information related to the medicine. Again, the transfer of pills into the container creates another opportunity for one or more pills to be lost, thereby not providing the proper amount to the consumer.

With some consumers, it may be difficult to remember which pill to take, when to take it, and even whether they have already taken the pill. To overcome this problem, an array pack was devised with a series of compartment resembling cups or blisters, each "blister" containing one or more pills that are to be taken at the same time. This form of packaging is known as "blister packs," "dose packs," "bingo cards," and "punch cards." Often, cold medicine is supplied to consumers on such a card with a single dose in each blister and then the blister pack is packaged in a simple box with labels and advertising on the outside. Although a huge benefit to the consumer, filling the blister pack with a prescription involves the Pharmacist sitting down and laboriously dispensing the doses by hand into the individual blisters of the pack, then sealing the back. Furthermore, for prescriptions in which the dosage varies by day, extra attention to detail is required because each blister may have different quantities of pills or pills of a different strength or a combination of such, again feeding into the probability of error.

Presently, automation equipment is available for automatically filling prescriptions from a plurality of pill storage bins (or cassettes). Each storage bin is filled with a supply of a given medicine in pill, capsule or gel-cap form. The storage bin has an electro-mechanical dispensing control and the dispensing control is controlled by a machine control that has, for example, a user interface for the Pharmacist to enter the medicine name, strength and quantity, thereby initiating the dispensing of that number of pills. The pills are then directed into a vial.

The art of filling containers with pills is quite old, going back to U.S. Pat. No. 2,457,220 to Fowler, et al filed Mar. 16, 1945 which is hereby incorporated by reference and describes a motorized pill dispensing machine. This machine has one storage area for a supply of pills that are thereafter handled by the machine in groups of a known quantity. As the machine rotates, the pills fall into receptacles numbering that known quantity, then as it further rotates, that number of pills falls through an opening, into a funnel and then into a pill container in the shape of a bottle or vial. This device is limited to dispensing a fixed quantity of a single type of pills into bottles.

U.S. Pat. No. 6,318,051 B1 to Preiss, PCT filed Dec. 30, 1996 which is hereby incorporated by reference describes a device for dispatching singular items from a single supply station into product packs (blister packs) of the same type and is useful in an assembly line process of filling blister packs with a single medication. This device is limited to dispensing a single type of pill into a single type of blister pack. Likewise, U.S. Pat. No. 6,805,259 B2 to Stevens, et al, PCT filed Jun. 1, 2001, hereby incorporated by reference, also describes a tablet dispenser that dispenses tablets from multiple reservoirs into blister packs. Although not limited to one medication as the previous patents, this device is limited to dispensing only into blister packs.

U.S. Pat. No. 6,925,774 B2 to Peterson, filed May 14, 2003 is hereby incorporated by reference. It describes a machine a machine for filling blister package cavities. This device does not fill vials and to do so, a pharmacy would need to purchase a second machine.

Unfortunately, the prior art does not have one dispensing apparatus that dispenses to either a vial or a punch card, requiring the pharmacy to purchase two independent dispensing machines, one for vials and the other for punch cards. Besides imposing a cost burden upon the pharmacy for two independent dispensers, the duplication of machines requires extra space, consumes more power and, where the same pills are stored in cassettes of both machines, dual supplies of those pills is required, increasing inventory. These issues often lead a pharmacy to select one packaging type over the other. That choice is usually the vial type, almost limiting the consumer to only receiving medication in vials; preventing the consumer from reaping the benefits of blister packs.

What is needed is a single apparatus that will accurately fill a prescription from a plurality of cassettes into either a vial or into a blister pack.

SUMMARY OF THE INVENTION

An object of the present invention is to provide a device that dispenses a quantity of pills or capsules into a vial.

Another objective of the present invention is to provide a device that dispenses a quantity of pills or capsules into a blister pack.

In one embodiment, a pill dispensing device is disclosed including at least one cassette for storing a supply of pills with a control for releasing a quantity of the pills from a selected cassette at a target location. A movable platen holds either a blister pack or a vial and is positioned to a first position such that a blister of the blister pack is located under the target location or to a second position such that the vial is located beneath the target location where the quantity of pills are deposited.

In another embodiment, a method of dispensing pills from a machine is disclosed. The machine is a dispensing machine with a movable platen for holding both a vial and a blister pack. The method includes moving a cassette filled with a supply of pills over a target location and selecting a quantity of pills to be dispensed. Next, a target package type is selected. If the target package type is a vial, then the vial is positioned beneath the target location and the quantity of pills is released from the cassette into the vial. If the target package type is a blister pack, then for each blister in the blister pack, that blister is positioned under the target location and a subset of the quantity of the pills is released from the cassette into the blister.

In another embodiment, a pill dispensing device is disclosed including a way to store a supply of pills and releasing a selected quantity of the pills to a target location. A movable platen adapted to hold both a blister pack and a vial is affixed to a device capable of positioning it at a first position such that a blister of the blister pack is located under the target location and for positioning it at a second position such that the vial is located beneath the target location.

In another embodiment, a movable platen is disclosed including a frame with a series of shaped openings that correspond to blisters of a blister pack and a device adapted to hold a vial.

BRIEF DESCRIPTION OF THE DRAWINGS

The invention can be best understood by those having ordinary skill in the art by reference to the following detailed description when considered in conjunction with the accompanying drawings in which.

DETAILED DESCRIPTION OF THE INVENTION

Reference will now be made in detail to the presently preferred embodiments of the invention, examples of which are illustrated in the accompanying drawings. Throughout the following detailed description, the same reference numerals refer to the same elements in all figures. Throughout the description (including the claims), the word "pill" is used generically. For the purpose of this application, the word pill is used to represent anything that can be dispensed by the device of the present invention and there is no limitation placed upon that which is dispensed. For example, tablets, capsules, caplets and gel-caps can be dispensed as well as coated candy (e.g., placebos). The present invention works well with most any solid object and can be scaled to work for much larger objects as well. Throughout the description (including the claims) the forms of packaging are referred to as vials or blister packs. For the purpose of this application, the word vial is used to represent any container having a single compartment for storing pills including, but not limited to, vials, bottles, tubes and the like. Often, these vials are configured to accept a lid that either snaps in place or screws in place. Blister packs refer to a class of packaging that has multiple compartments, wherein each compartment stores a dose of one or more pills, either the same pills or different pills. Other names for blister packs are, for example, dose packs, bingo cards and punch cards. The individual blisters of the blister pack can be arranged in any fashion, such as a linear series of blisters and a matrix of blisters and may be evenly spaced or not. Often, blister packs are sealed by a thin sheet that adheres to their open side, allowing one blister at a time to be pierced to gain access to the pills within that blister.

Figure 1:
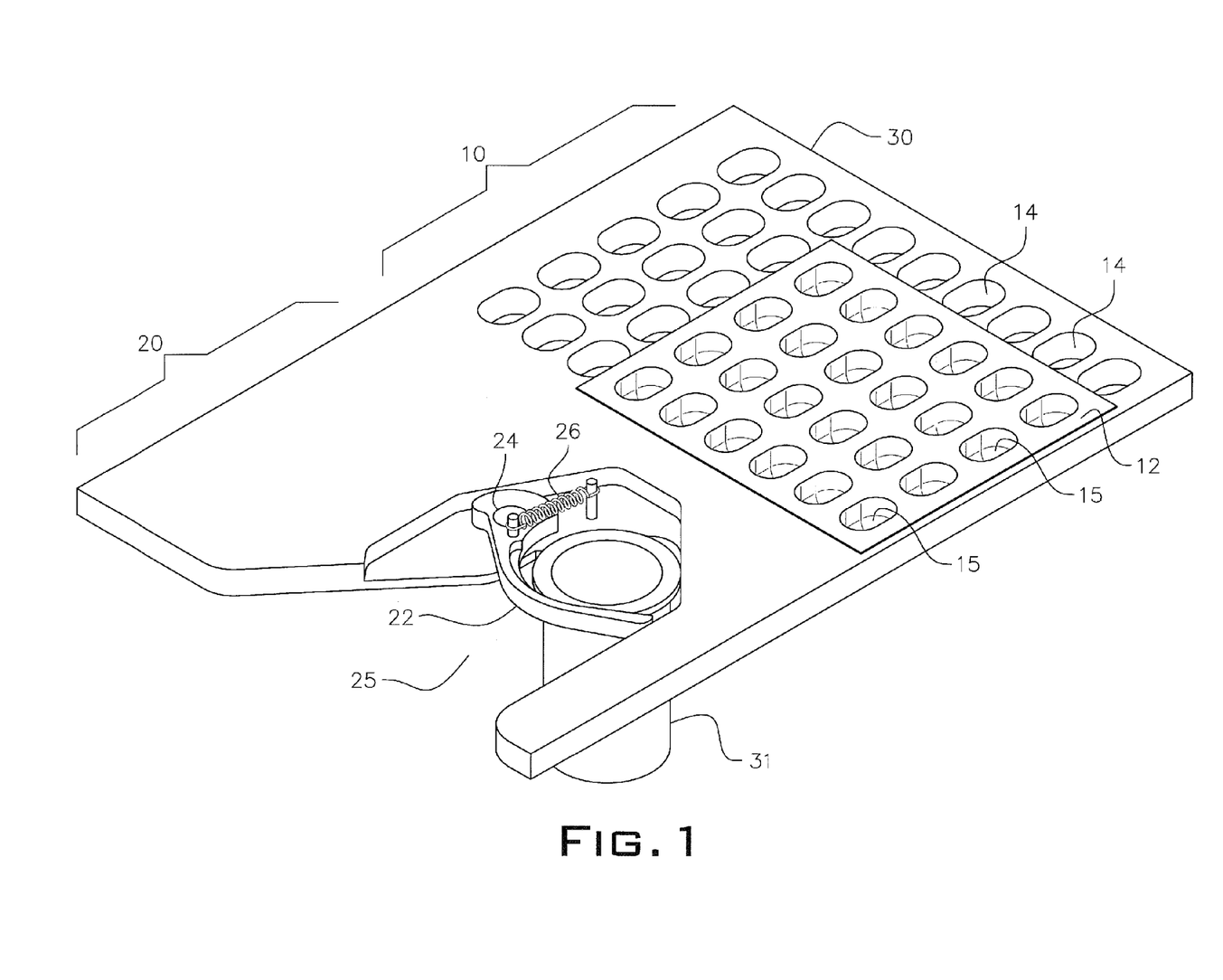
FIG. 1 illustrates a top plan view of a platen of a first embodiment of the present invention.

Referring to FIG. 1, a top plan view of a platen of a first embodiment of the present invention is shown. The platen frame 30 is made from a substantially flat material. In the preferred embodiment, the platen frame 30 is made from a metal such as steel but in other embodiments, the platen frame 30 is made from a hard plastic. The platen frame 30 has an area for accepting a blister pack 10 and an area for accepting a vial 20. The area for accepting a blister pack 10 has a plurality of holes or indentations 14 in which the individual blisters 15 of a blister pack 12 rest, thereby holding the blister pack 12 in place. In some embodiments, holes 14 are bored through the platen frame 30 while in other embodiments, indentations 14 are carved or formed in the platen frame 30. In one embodiment, the number of holes or indentations 14 matches the number of blisters 15 in the blister pack 12 while in other embodiments, the number of holes or indentations 14 exceed the number of blisters 15 in the blister pack 12. In one embodiment, one or more larger holes or indentations 14 cover an area large enough for more than one of the blisters 15 of a blister pack 12 to rest within it.

The area for accepting vials 20 has a receptacle for holding a vial 31. In one embodiment, the receptacle includes a cut out area 25 in the platen frame 30 and an arm 22 for holding the vial 31. The arm 22 is attached to the platen frame 30 with a pivot 24 and is spring loaded in the direction towards the platen frame 30 by a spring 26 so that the arm can be pulled out by an operator and when released, places a force against the vial 31. This is an example of vial holding designs and many other designs are anticipated by the present invention and known in the art. For example, instead of the cut out 25, a hole is cut in the platen frame 30 sized to fit the outside diameter of the vial 31 for holding the vial 31, but has the limitation that it can only hold one size vial 31.

Figure 2:
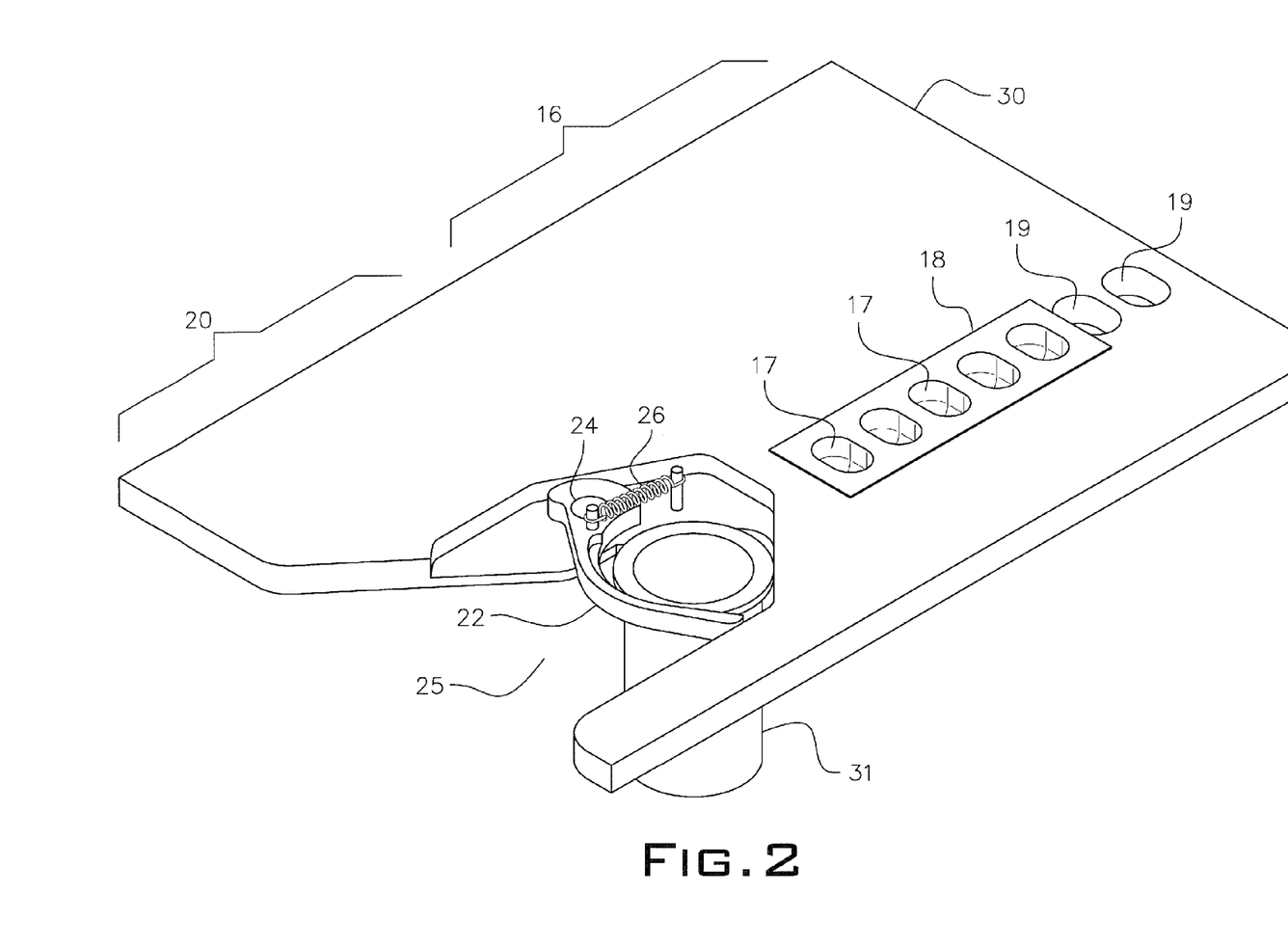
FIG. 2 illustrates a top plan view of a platen of a second embodiment of the present invention.

Referring to FIG. 2, a top plan view of a platen of a second embodiment of the present invention is shown. As in the first embodiment platen frame 30 is a substantially flat platform. In the preferred embodiment, the platen frame 30 is made from a metal such as steel but in other embodiments, the platen frame 30 is made from a hard plastic. The platen frame 30 has an area for accepting a blister pack 16 and an area for accepting a vial 20. The area for accepting a blister pack 16 has a plurality of holes or indentations 19 in which the individual blisters 17 of a blister pack 18 rest, thereby holding the blister pack 18 in place. In some embodiments, holes 19 are bored through the platen frame 30 while in other embodiments, indentations 19 are carved or formed in the platen frame 30. In one embodiment, the number of holes or indentations 19 matches the number of blisters 17 in the blister pack 18 while in other embodiments, the number of holes or indentations 19 exceed the number of blisters 17 in the blister pack 18. In one embodiment, one or more large holes or indentations 19 cover an area large enough for more than one blister 17 of a blister pack 18 to rest within. In this embodiment, the blisters 17 are arranged in a single row. This arrangement accommodates blister packs 18 that have a small number of blisters, for example seven, one for each day of the week. In one embodiment, it is preferred, but not required, that the center of each hole or indentation 19 correspond to the center of the vial 31 so that the platen need only be moved in one direction when changing between blister packs 18 and a vial 31.

The location for accepting vials 20 has a receptacle for holding the vial 31 while it is being filled. In one embodiment, the receptacle includes a cut out area 25 in the platen frame 30 and an arm 22 for holding the vial 31. The arm 22 is attached to the platen frame 30 with a pivot 24 and is spring loaded in the direction towards the platen frame 30 by a spring 26 so that the arm can be pulled out by an operator and when released, places a force against the vial 31.

Figure 3:
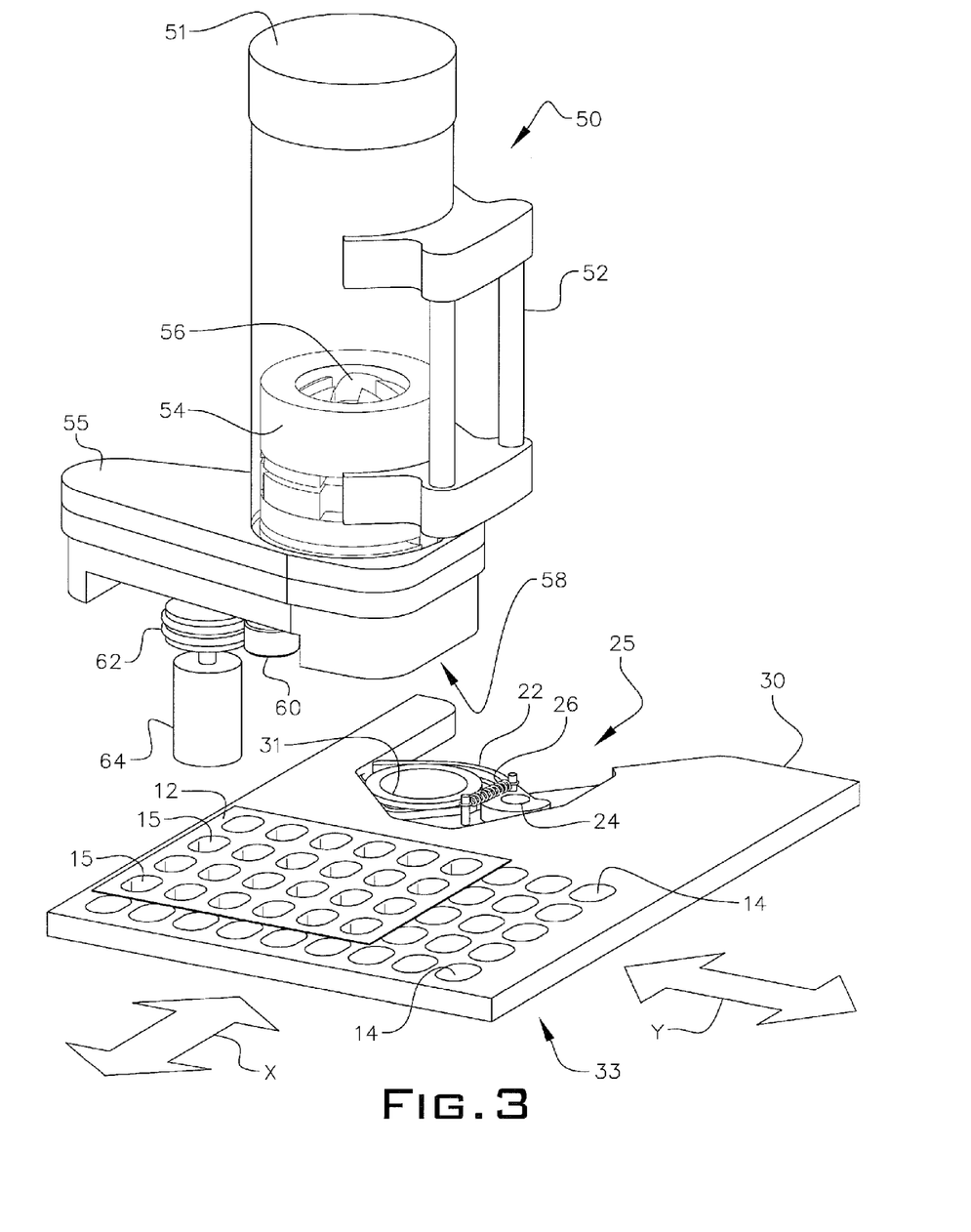
FIG. 3 illustrates a perspective view of the first embodiment of the present invention with a dispensing unit.

Referring to FIG. 3, a perspective view of the first embodiment of the present invention with a cassette dispensing unit is shown. The movable platen 33 is a platen as described in the previous description and is movable in at least one direction under the control of at least one drive mechanism. In some embodiments, the drive mechanism is one or two servo motors, moving the movable platen 33 in either an X direction or and X and Y direction. A movable platen 33 designed to hold a blister pack 18 with a single row of blisters need only move in an X direction (see FIG. 2) while a movable platen 33 designed to hold a blister pack 12 with multiple rows, each having multiple blisters, moves in both an X and Y direction to index to each of the blisters. In other embodiments, the control mechanism is one or two motors and one or two worm gears. There are many ways known in the art to accurately drive a surface such as the movable platen 33 in both an X direction and a Y direction and are all anticipated by the present invention.

In FIG. 3, the platen 33 moves in the X direction and the Y direction to position either one of the blisters or the vial beneath a target location 58 of a cassette 50 filled with pills. This position is referred to as the target location because the pills drop from the cassette 50 into whatever is positioned under this location. Once positioned to the target location 58, the cassette 50 is controlled to drop a required quantity of pills and, since the desired blister 15 or vial 31 is positioned directly beneath the target location, the pills drop into either the blister 15 or the vial 31.

The cassette 50 is shown for completeness and can be any form of dispensing device known in the industry, including the Cassette for Dispensing Pills as described in a co-pending patent application. In that application, cassette 50 has a handle 52 to enable an operator or a robot to remove the cassette from the automated filling machine (not shown) and a lid 51 to keep pills in and contaminates out of the cassette 50. The pills in the cassette are funneled toward a dome-shaped vane 56 by a cassette vane top ring 54 and into an indexing mechanism that dispenses pills in single file, periodically, as the cassette drive wheel 60 is rotated by a motor 64 and a motor drive wheel 62. The gear housing 55 holds the gear system used to drive the indexing mechanism that is coupled to a drive wheel 60. This is a simplified description of an exemplary mechanism for dispensing a known quantity of pills to a specific location and many other mechanisms for dispensing pills to a specific location are known in the art. One such mechanism includes a cassette for holding the pills and a shutter mechanism that opens to drop a single pill to the target location.

Figure 4:
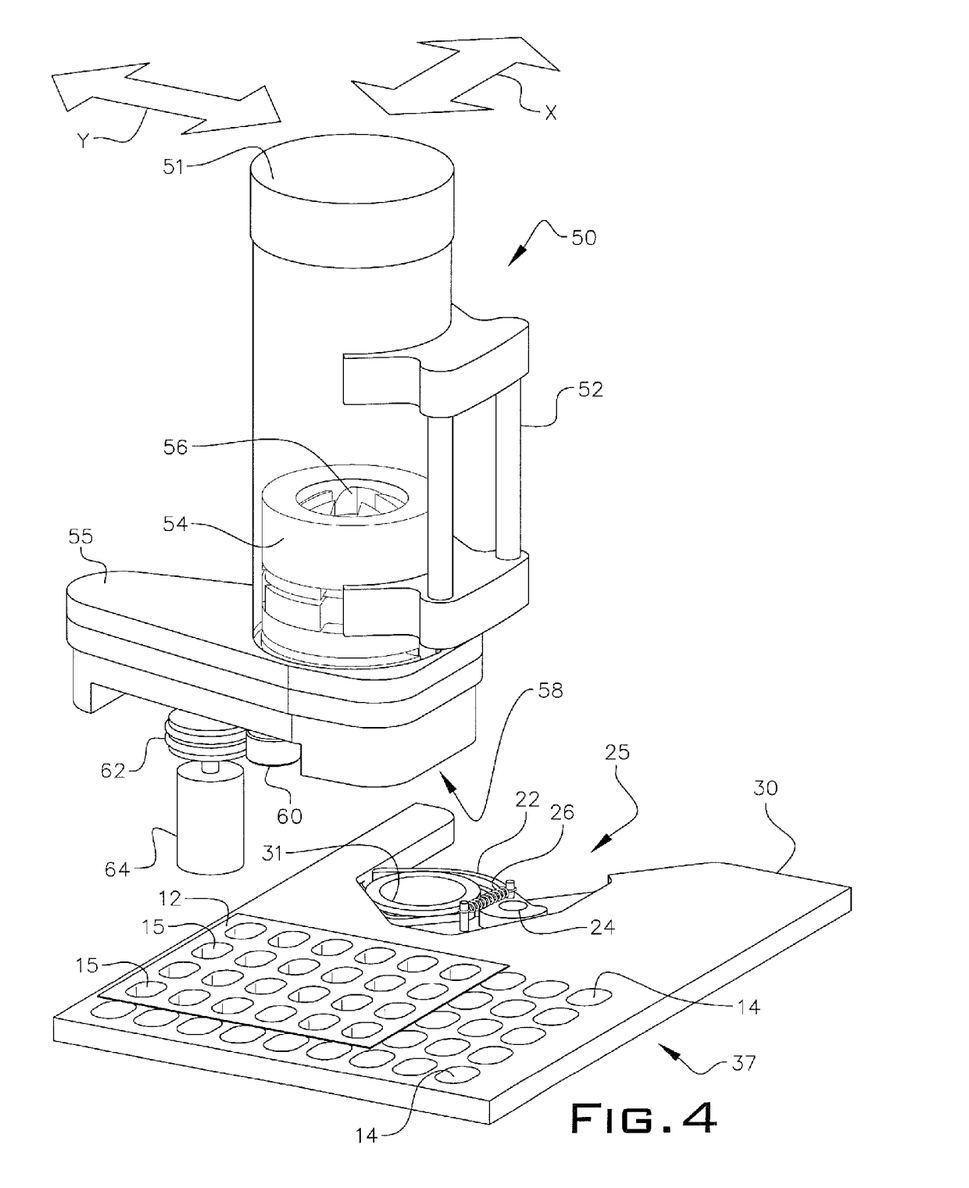
FIG. 4 illustrates a perspective view of a third embodiment of the present invention with a movable cassette.

Referring to FIG. 4, a perspective view of a third embodiment of the present invention with a movable cassette dispensing unit is shown. The platen 37 is a platen as described in the previous description except that in this embodiment, the platen 37 is stationary. Instead of moving the platen 37, the drive mechanism moves the cassette and in some embodiments, moves the entire cassette carousel, thereby positioning the dispensing cassette 50 over the target blister 15 or vial 31. In some embodiments, the control mechanism is one or two servo motors, moving the cassette 50 in either an X direction or an X and Y direction. If the stationary platen 37 is designed to hold a blister pack 12 with a single row of blisters 15 (see FIG. 2), the control mechanism need only move in an X direction while if the stationary platen 37 is designed to hold a blister pack 12 with multiple rows, each having multiple blisters 15, then the control mechanism needs to move the cassette in an X and Y direction to index to each of the blisters. In one embodiment, the control mechanism is one or two motors and one or two worm gears. There are many ways known in the art to accurately drive an object such as the cassette 50 in both an X direction and a Y direction and are all anticipated by the present invention.

In FIG. 4, the cassette 50 moves in the X direction and the Y direction to position either one of the blisters 15 or the vial 31 beneath a cassette 50 filled with pills. This position is referred to as the target location 58. Once the cassette is positioned to the target location 58, the cassette 50 is controlled to drop a required quantity of pills and since the desired blister 15 or vial 31 is positioned directly beneath the target location 58, the pills drop into either the blister 15 or the vial 31.

The cassette 50 is shown for completeness and can be any form of dispensing device known in the industry, including the Cassette for Dispensing Pills as described in a co-pending patent application. In that application, cassette 50 has a handle 52 to enable an operator or a robot to remove the cassette from the automated filling machine (not shown) and a lid 51 keeping pills in and contaminates out of the cassette 50. The pills in the cassette are funneled toward a dome-shaped vane 56 by a cassette vane top ring 54 and into an indexing mechanism that dispenses pills in single file, periodically as the cassette drive wheel 60 is rotated by a motor 64 and a motor drive wheel 62. This is a simplified description of an exemplary mechanism for dispensing a known quantity of pills to a specific location and many other mechanisms for dispensing pills to a specific location are known in the art. One such mechanism includes a cassette for holding the pills and a shutter mechanism that opens to drop a single pill to the target location.

Figure 5:
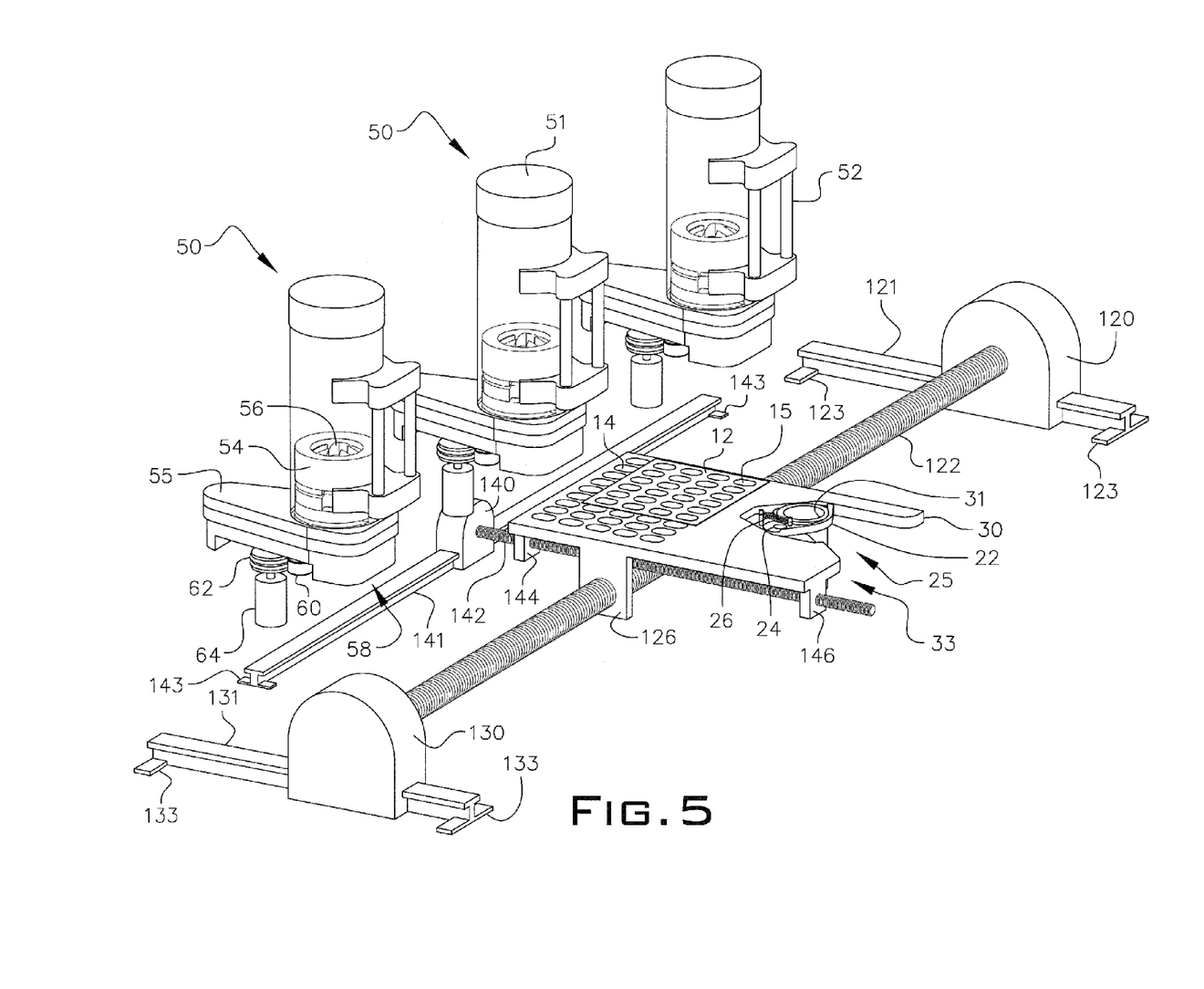
FIG. 5 illustrates a perspective view of a fourth embodiment of the present invention with a linear dispensing unit.

Referring to FIG. 5, a perspective view of a fourth embodiment of the present invention with a linear dispensing unit is shown. In this embodiment, the movable platen 33 is driven in an X direction by a first motor 120 coupled to a threaded shaft 122. The threaded shaft 122 is long enough to allow the movable platen 33 to travel under a plurality of cassettes 50. In one embodiment, the threaded shaft 122 is held at an end distal to the first motor 120 by a support 130. The first motor 120 and the support 130 freely travel in the y direction by way of rails 121/131. The rails are held in place by anchors 123/133. The threaded shaft 122 interfaces to the platen 33 at a linkage 126 that pulls or pushes the platen 33 along the length of the threaded shaft 122; thereby creating what is known as a worm gear. The cassettes 50 are similar to the previously described cassette, but each cassette in this embodiment has a separate drive motor 64 to cause the dispensing of pills. The first motor 120 is capable of positioning the platen 33 such that the vial 31 or an individual row of blisters 14 align with the target location 58 beneath a selected cassette 50. A second motor 140 travels with the platen 33 in the X direction along another rail 141, the rail is held in place by anchors 143. The second motor 140 positions the platen 33 in the Y direction, so that an individual blister 14 or the vial can be positioned under the target location, at which time, the required number of pills are dropped from the cassette 50. The second motor 140 is coupled to a second threaded shaft 142 that interfaces with the movable platen 33 at linkages 144/146. Either or both of the linkages 144/146 are threaded to mate with the threaded shaft 142 or are bearings. The threaded shaft 142 and the linkages 144/146 form what is known as a worm gear. The mechanism described is just one example of a method of moving a platform in both an X and a Y direction and many others are known in the art.

Figure 6:
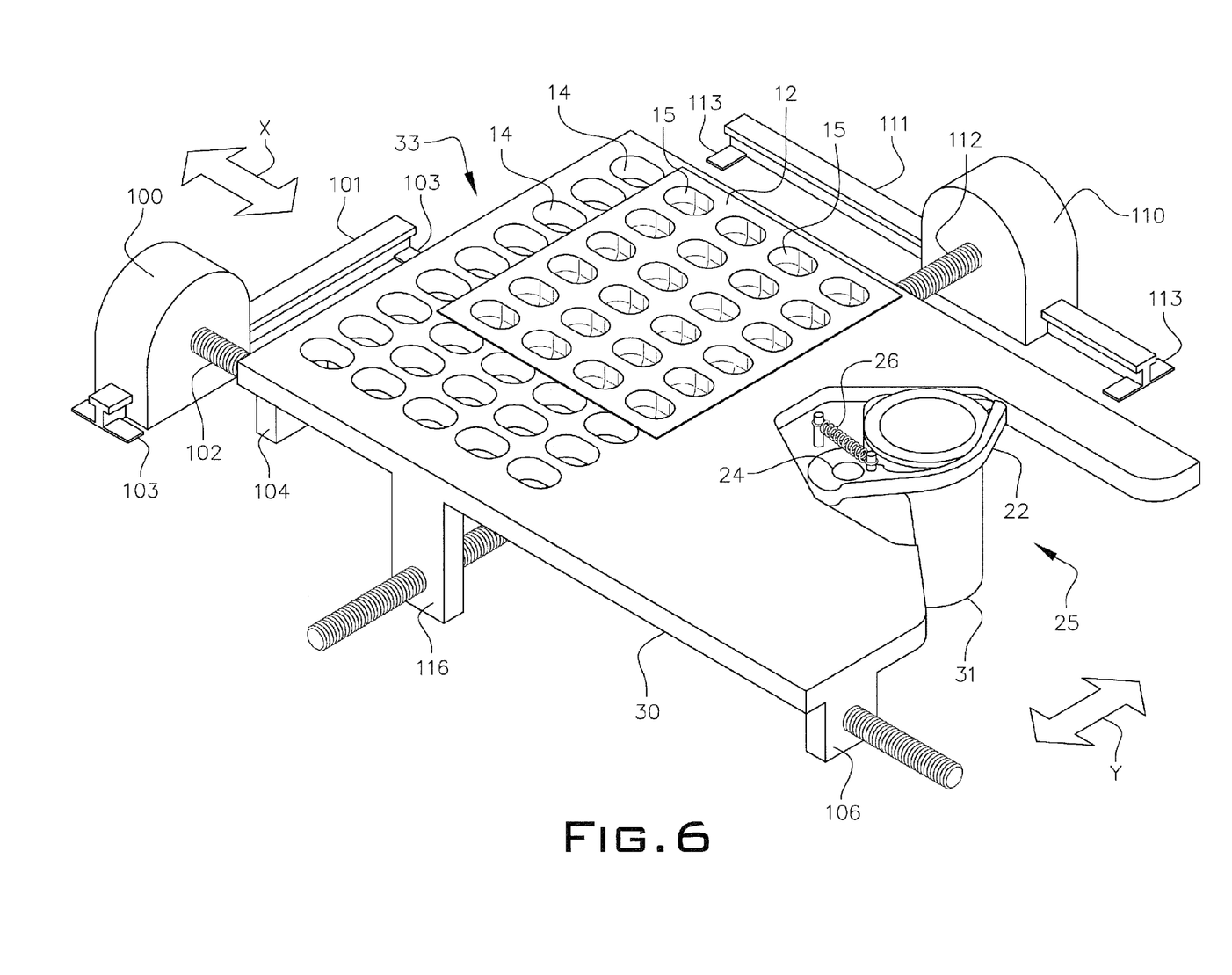
FIG. 6 illustrates a perspective view of the first embodiment of the present invention showing an example of a servo motor drive.

Referring to FIG. 6, a perspective view of the first embodiment of the present invention showing an example of a servo motor drive is shown. The movable platen 33 is made from a substantially flat frame 30. The frame 30 has a plurality of holes or indentations 14 in which the individual blisters of a blister pack 12 rest, thereby holding the blister pack 12 in place. In some embodiments, holes 14 are bored through the frame 30 while in other embodiments, indentations 14 are carved or formed in the frame 30. In this embodiment, the receptacle for holding a vial 31 includes a cut out area 25 in the frame 30 and an arm 22 for holding the vial 31. The arm 22 is attached to the frame 30 with a pivot 24 and is spring loaded in the direction towards the frame 30 by a spring 26 so that the arm can be pulled out by an operator and when released, places a force against the vial 31. In this embodiment, an X servo motor 100 moves the frame 30 in an X direction by turning a threaded shaft 102, in which the threads pass through a threaded opening 104 affixed to the frame 30, thereby forming a worm gear. A distal end of the threaded shaft 102 is supported in some embodiments by a bearing or a threaded opening 106. Also, in this embodiment, a Y servo motor 110 moves the frame 30 in a Y direction by turning a second threaded shaft 112, in which the threads pass through a threaded opening 116 affixed to the frame 30, thereby forming a second worm gear. The X servo motor 100 moves freely in the Y direction along a rail 101 and the rail is held in place by anchors 103. The Y servo motor 110 moves freely in the X direction along a rail 111 and that rail is held in place by anchors 113. In some embodiments, the threaded shaft 112 is supported by a bearing or second threaded opening (not shown).

Figure 7:
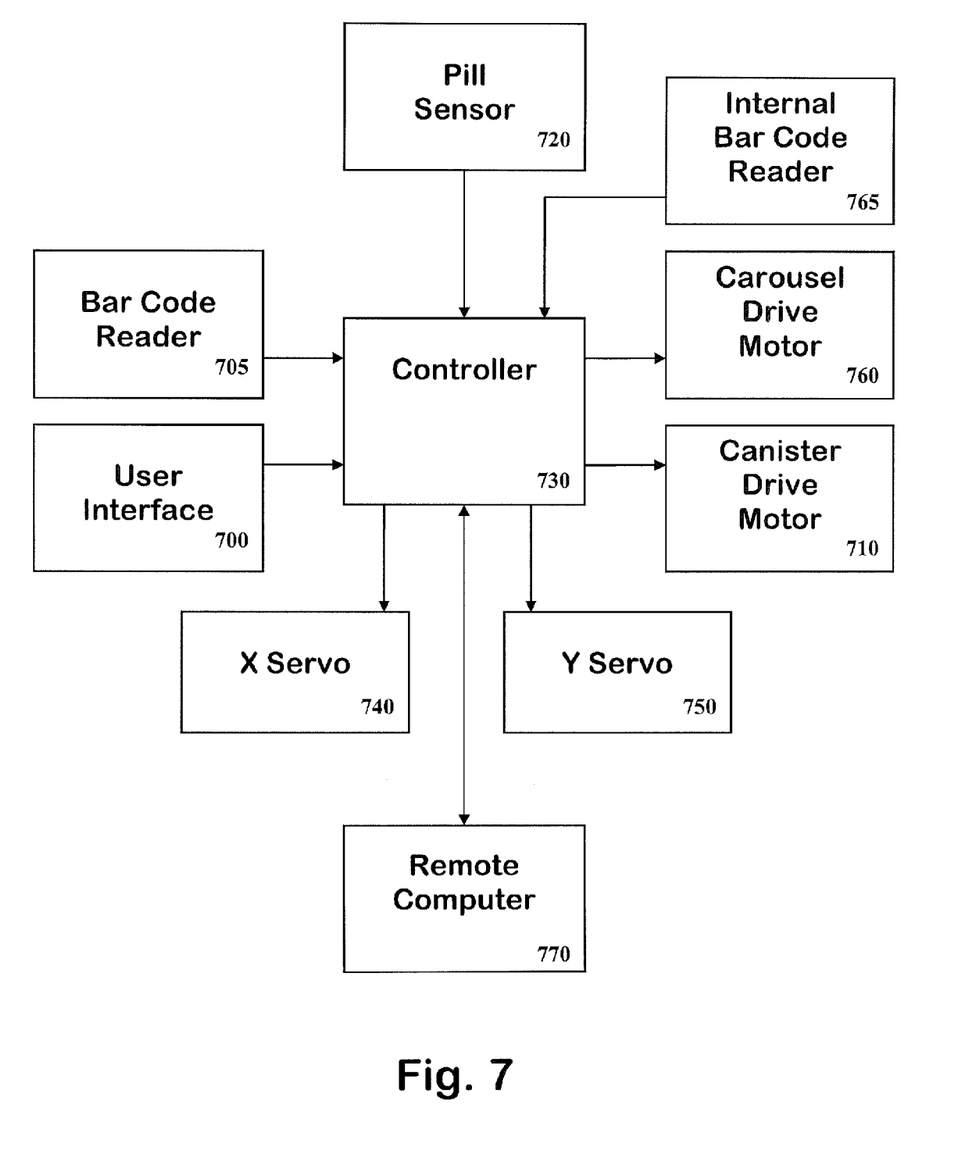
FIG. 7 illustrates a block diagram of the control system of the present invention.

Referring to FIG. 7, a block diagram of the electrical system of the present invention is shown. The controller 730 accepts inputs from the user interface 700, from the bar code reader 705 or from a remote computer 770. Although many commands and operations are present in most embodiments, the commands of interest to the present invention include dispensing a certain quantity of a pill into a package. In most embodiments, requests to dispense pills coming from the bar code reader 705 or the remote computer 770 include a National Drug Code (NDC) identifying the drug to dispense; a quantity; and a package type. The type of package specified is either a vial or blister pack. Once information regarding the medication, the quantity and the desired packaging is ascertained, the cassette containing the medication is moved to the target location using, for example, the carousel drive motor 760. In some embodiments, an internal bar code reader 765 reads a bar code on the cassette to make sure the correct cassette is in position to fill the prescription. The package is filled using the cassette drive motor 710 to dispense the quantity of pills over a target location. The pill sensor 720 counts the pills and the X-servo 740 and Y-Servo 750 position the packaging under the cassette, allowing the pills to fall into the correct package (either the vial or a blister of the blister pack). If the packaging is a blister pack, the X-servo 740 and Y-Servo 750 are used to step the package in an X and Y direction, sequentially positioning each blister under the cassette to deliver the pill(s) into the individual blisters. In some embodiments (not shown) additional servo motors are deployed to control the machine in different ways, allowing for an increased number of cassettes and/or packaging stations. Details on these are left out to clearly define the inventive part of the present invention. Details of the system operations are described with FIG. 8 and 9. Note that in this embodiment, the cassettes are located on a carousel but the present invention is not limited to any specific method of positioning the pill supply over the target packaging. For example, in another embodiment, the pill supply cassettes are arranged in linear fashion and instead of a carousel drive, a linear drive such as a worm gear is used to position the cassette. In some embodiments, vertical stacking is used, but care must be taken to limit contamination of one medicine to another.

Figure 8:
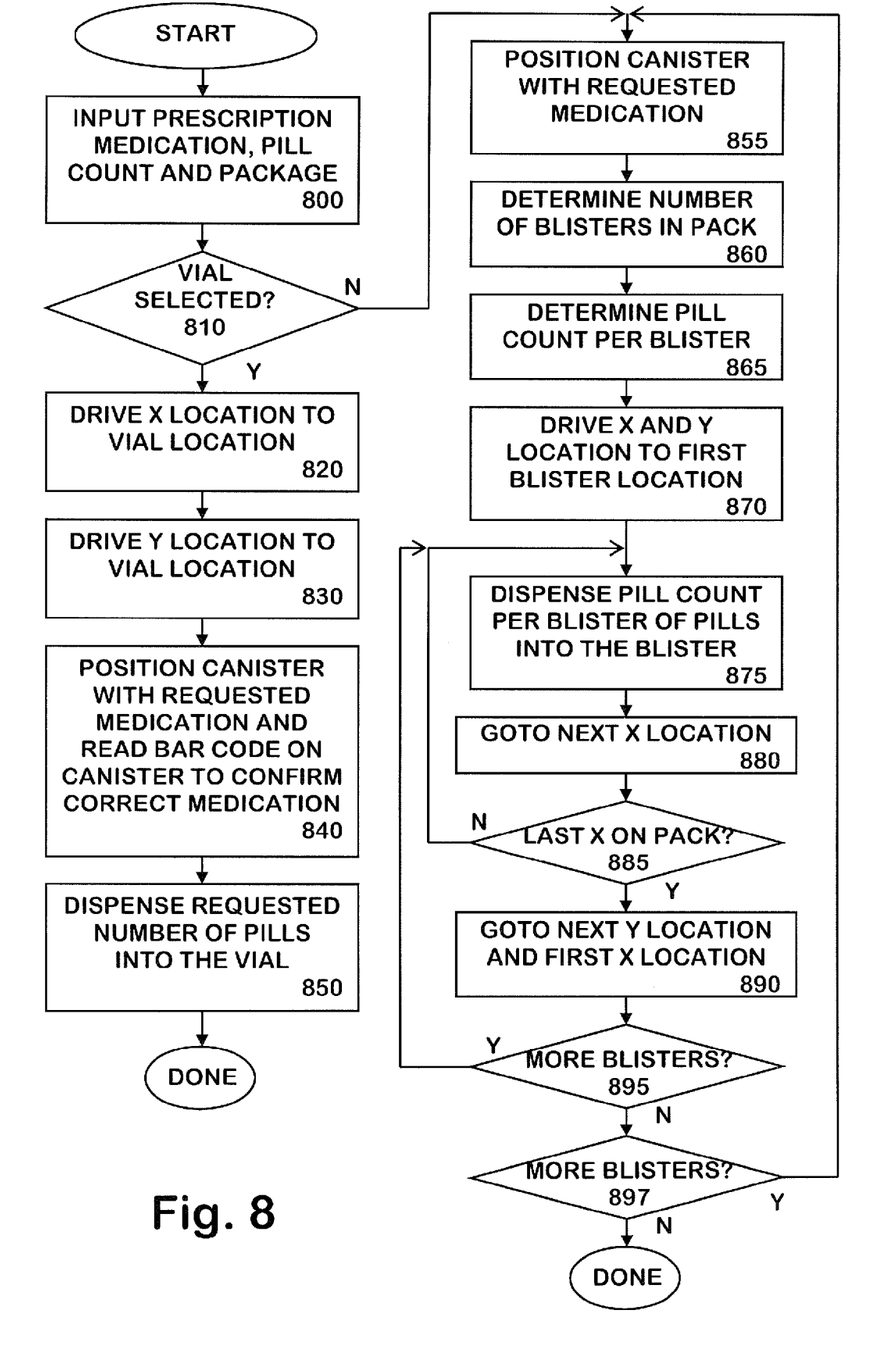
FIG. 8 illustrates a flow chart of the control system of the present invention.

Referring to FIG. 8, a flow chart of the operation of the present invention is shown. As in FIG. 7, the prescribed medication, pill count and target packaging is obtained 800 from a user interface 700, read from the bar code reader 705 or imported from the remote computer 770. If the packaging selected is a vial 810, then the X-servo 740 is used to move the platen in the X direction 820 and the Y-servo 750 is used to move the platen in the Y direction 820 to a position where the vial will be at the target location. Then the cassette with the requested pill is positioned over the vial 840 and the correct number of pills is dispensed into the vial 850. Details of pill dispensing are described in FIG. 9. In some embodiments, a bar code on the cassette is read 840 by the internal bar code reader 765 as a safety precaution to make sure the correct medicine is dispensed.

If the packaging selected is not a vial 810 (e.g., it is a blister pack), then the cassette with the requested pill is positioned over the target location 855. The number of blisters in the blister pack is determined 860 and, either from the number of blisters or a number included in the input data, the number of pills per blister is determined 865. In one embodiment, the number of pills per blister is set to one. In another embodiment, the number of pills per blister is set to the total number of pills to be dispensed divided by the total number of blisters. After that, the X-servo 740 is used to move the platen in the X direction and the Y-servo 750 is used to move the platen in the Y direction to a position where the first blister is at the target location 870. The correct number of pills is dispensed into the blister at the dispensing location 875. Details of pill dispensing are described in FIG. 9. Next, the platen is positioned so the next blister is under the target location (next in the X direction) 880 and it is determined if that location is beyond the end of the blister pack 885. If it is not at the end of the blister pack, then the prior three steps (875-885) are repeated until an end is reached. Once at the end, the platen is positioned so the first blister (first X) of the next row of blisters (next Y) is under the target location 890. If there is another row on the blister pack 895, then the previous 5 steps are repeated (875-895) filling that row and any other rows. If there isn't another row, then the process of filling the blister pack with a first medication is finished. If there is another medication to fill into the blister pack 897, then the previous ten steps (855-897) are repeated for the next medication until all required medications are inserted into each blister of the blister pack. In other embodiments, some of the steps are performed in different order.

Figure 9:
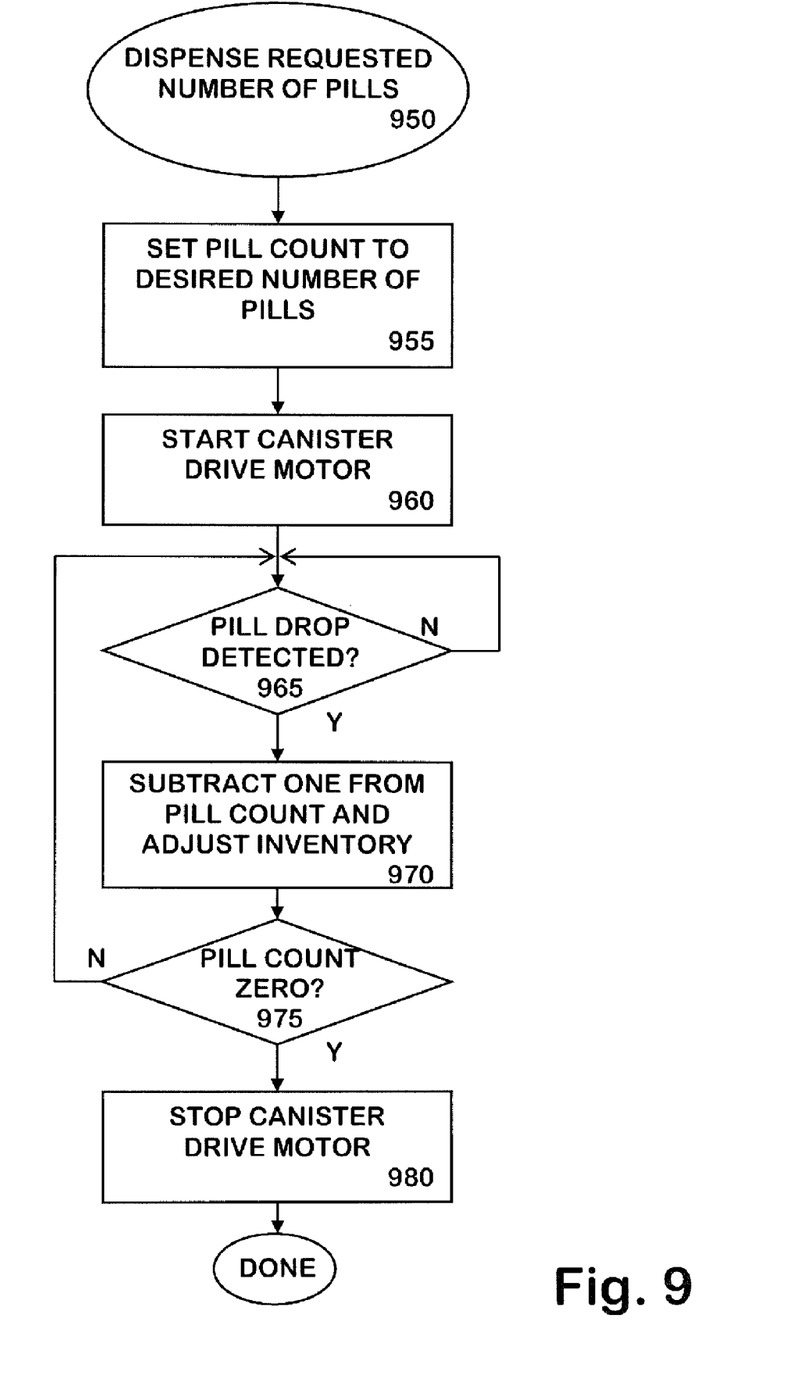
FIG. 9 illustrates a second flow chart of the control system of the present invention.

Referring to FIG. 9, a flow chart of the operation of filling a requested number of pills 950 of the present invention is shown. A counter is set to the desired number of pills 955 and the cassette drive motor is started 960. In the operation of this embodiment, the cassette drive motor operates a start/stop gear within the cassette, such that the continuous rotation of the motor is converted into a rotate/pause cycle of the cassette and at each pause, one pill should fall from the cassette at the target location. In other embodiments, other mechanisms are used to drop a pill from a cassette including electromagnetic shutters and the like. These alternate embodiments will also work as this is a sample process for dropping a known quantity of pills. Continuing, a detection loop waiting for a signal that a pill has dropped loops until a pill drop is detected 965. Note, pill drop detectors are known in the industry, one example is a light source and light detector, whereby the pill interferes with the light, thereby creating an electrical signal at the detector.

Once a pill drop has been detected 965, the pill count is decremented 970 and in some embodiments, the inventory adjusted 970. In some embodiments, an inventory of the contents of each cassette is maintained, and if so, at this point the inventory is adjusted to reflect one pill being removed from the inventory. If the pill count is still not zero 975, the previous three steps (965-975) are repeated until the correct count of pills has been counted, at which time the cassette drive motor is stopped 980.

Equivalent elements can be substituted for the ones set forth above such that they perform in substantially the same manner in substantially the same way for achieving substantially the same result.

It is believed that the system and method of the present invention and many of its attendant advantages will be understood by the foregoing description. It is also believed that it will be apparent that various changes may be made in the form, construction and arrangement of the components thereof without departing from the scope and spirit of the invention or without sacrificing all of its material advantages. The form herein before described being merely exemplary and explanatory embodiment thereof. It is the intention of the following claims to encompass and include such changes.

What is claimed is:

1. A method of dispensing pills from a machine having a platen that is movable, the platen holding a target packet of either a vial or a blister pack, the method comprising:
   moving a cassette over a target location, the cassette having a designated supply of pills within;
   selecting a quantity of the pills to be dispensed from the cassette;
   determining a type of the target package held in the platen;
   if the type of target package is the vial:
     positioning the vial by moving the platen holding the vial beneath the target location;
     releasing the quantity of the pills from the cassette into the vial; and
   if the type of target package is the blister pack; for each blister in the blister pack:
     positioning the each blister under the target location by moving the platen holding the blister pack;
     releasing a subset of the quantity of the pills from the cassette into the each blister.

2. The method of dispensing pills of claim 1, wherein the type of package is the blister pack and the subset of the quantity of the pills is one pill.

3. The method of dispensing pills of claim 1, wherein the type of package is the blister pack and the subset of the quantity of the pills is the quantity of the pills divided by a number of blisters in the blister pack.

4. The method of dispensing pills of claim 1, wherein the type of package is the blister pack and the positioning is performed by moving the platen in an X direction and in a Y direction.

5. The method of dispensing pills of claim 1, wherein the type of package is the blister pack and the positioning is performed by moving the cassette in an X direction and in a Y direction.

6. The method of claim 1, wherein the step of determining the type of target package includes reading a bar code.

* * * * *